United States Patent
Kuo et al.

(10) Patent No.: US 9,757,393 B2
(45) Date of Patent: Sep. 12, 2017

(54) **DERIVATIVES OF ERGOSTATRIEN-3-β-OL FROM *ANTRODIA CAMPHORATA* AND ANTIGLYCEMIC, ANTIHYPERLIPIDEMIC AND DECREASING HEPATIC FAT USE THEREOF**

(71) Applicant: Chun-Ching Shih, Taichung (TW)

(72) Inventors: Yueh-Hsiung Kuo, Taichung (TW); Chun-Ching Shih, Taichung (TW); Cheng-Hsiu Lin, Taichung (TW)

(73) Assignee: Chun-Ching Shih, Taichung (TW)

( * ) Notice: Subject to any disclaimer, the term of this patent is extended or adjusted under 35 U.S.C. 154(b) by 0 days.

(21) Appl. No.: 15/011,342

(22) Filed: Jan. 29, 2016

(65) Prior Publication Data

US 2017/0049787 A1 Feb. 23, 2017

(30) Foreign Application Priority Data

Aug. 17, 2015 (TW) .............................. 104126669 A

(51) Int. Cl.
*A61K 31/56* (2006.01)
*A61K 31/575* (2006.01)
*A61K 36/07* (2006.01)

(52) U.S. Cl.
CPC ............ *A61K 31/575* (2013.01); *A61K 36/07* (2013.01); *Y02P 20/582* (2015.11)

(58) Field of Classification Search
USPC ........................................................ 514/179
See application file for complete search history.

(56) References Cited

U.S. PATENT DOCUMENTS 5,023,250 A * 6/1991 Adams ...................... C07J 9/00
514/179

OTHER PUBLICATIONS

Y-H Kuo et al., "Ergostatrien-3β-ol from *Antrodia camphorata* Inhibits Diabetes and Hyperlipidemia in High-Fat-Diet Treated Mice via Regulation of Hepatic Related Genes, Glucose Transporter 4, and AMP-Activated Protein Kinase Phosphorylation," Journal of Agricultural and Food Chemistry, 2015, 63 (9), pp. 2479-2489.

* cited by examiner

*Primary Examiner* — Rei-Tsang Shiao
(74) *Attorney, Agent, or Firm* — Wang Law Firm, Inc.

(57) ABSTRACT

The present invention provides a method for treating diabetes, hyperlipidemia or hepatic total lipids by using ergostatrien-3β-ol and its derivatives, as well as a method for decreasing blood glucose and HbA1c levels and reducing blood total cholesterol and triglyceride levels, whereas increasing blood HDL-C levels; and a method for decreasing hepatic total lipid and triacylglycerol levels; and increasing expression levels of membrane glucose transporter 4 (GLUT4) and phospho-Akt in skeletal muscle tissue, and phospho-AMPK in both skeletal muscle and liver tissue using ergostatrien-3β-ol and its derivatives.

7 Claims, 11 Drawing Sheets

DERIVATIVES OF ERGOSTATRIEN-3-β-OL FROM *ANTRODIA CAMPHORATA* AND ANTIGLYCEMIC, ANTIHYPERLIPIDEMIC AND DECREASING HEPATIC FAT USE THEREOF

CROSS-REFERENCE TO RELATED APPLICATION

This application claims the priority of Taiwanese patent application No. 104126669, filed on Aug. 17, 2015, which is incorporated herewith by reference.

BACKGROUND OF THE INVENTION

1. Field of the Invention

The present invention relates to a method of suppressing diabetes, hyperlipidemia, or hepatic total lipids. Specifically, the invention relates to a method of suppressing diabetes, hyperlipidemia, or hepatic total lipids with ergostatrien-3β-ol (ergosta-7,9(11),22-trien-3β-ol) and its derivatives obtained from *Antrodia camphorata*. The ergostatrien-3β-ol and its derivatives from *Antrodia camphorata* are prepared using methanol extraction.

2. The Prior Art

Epidemiological analysis has predicted that the prevalence of Type 2 diabetes will reach 300 million by 2025. Type 2 diabetes mellitus represents greater than 90% of all cases and is characterized by hyperglycemia that involves either abnormalities in insulin secretion or insensitivity to insulin action at peripheral tissues, including adipose tissue, skeletal muscle, and liver tissues, which is known as insulin resistance. The development of insulin resistance is related to both genetic and environmental factors. The diet composition plays a key role in environmental factors.

The fruiting body of *Antrodia camphorata* is a well-known traditional Chinese mushroom in Taiwan and belongs to Polyporaceae (Aphyllophorales). The fruiting body, cultured mycelia, and spores are medicinal parts. Due to its rareness and difficulty in cultivation, *A. camphorata* is precious. Currently, *A. camphorata* is mainly obtained in the form of mycelia from submerged culture and used in the formation of nutraceuticals and functional foods. The fruiting body and cultured mycelia are composed of fatty acids, lignans, phenyl derivatives, sesquiterpenes, steroids, and triterpenoids. The fermented culture broth displayed cytotoxic activity, anti-inflammation, and vasorelation. The filtrate in submerged culture shows protective activity against $CCl_4$-induced hepatic toxicity and antioxidant property. However, the antidiabetic and anti-hyperlipidemic effects of the filtrate obtained from *A. camphorata* are not well-defined in high-fat diet (HFD)-induced diabetic mice.

SUMMARY OF THE INVENTION

The present invention provides a *Antrodia camphorata* extracts, which is an active component, ergostatrien-3β-ol and its derivatives, extracted from a freeze-dried powder of *A. camphorata*: extracting the freeze-dried powder of *A. camphorata* of the submerged whole broth three times with methanol at room temperature to obtain a methanol extract; evaporating the methanol extract in vacuo to obtain a brown residue; suspending the brown residue in $H_2O$ and partitioning the brown residue with ethyl acetate to obtain a EtOAc fraction; isolating the EtOAc fraction on a silica gel column chromatography; eluting the EtOAc fraction with a mixture of hexane and EtOAc to increase polarity; further purifying the EtOAc fraction with high performance liquid chromatography (HPLC) to obtain a raw product; eluting the raw product with 10% EtOAc in hexane; and recrystallizing the raw product with a acetone to obtain ergostatrien-3β-ol and its derivatives.

Accordingly, the present invention provides ergostatrien-3β-ol and its derivatives extracted from *A. camphorata*, which administrated to a subject with high-fat diet-induced insulin resistance and hyperlipidemia has following effects.

A primary objective of the present invention is to provide a method for treating diabetes, hyperlipidemia or hepatic total lipids, comprising administering to a subject in need thereof an effective amount of compounds represented by formula (I)

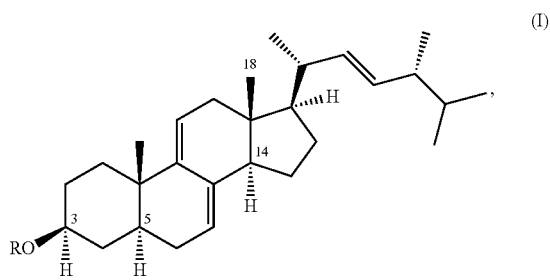

wherein R is a hydrogen atom,

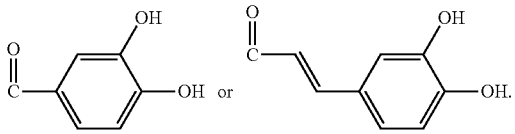

Another objective of the present invention is to provide a method for decreasing mRNA levels of phosphoenol pyruvate carboxykinase (PEPCK), glucose-6-phosphatase (G6 Pase), sterol regulatory element binding protein 1c (SREBP1c), diacylglycerol acyltransferase 2 (DGAT2), apolipoprotein C-III (apo C-III), and SREBP2, but increasing mRNA levels of apolipopretein A-I (apo A-I) and peroxisome proliferator activated receptor α (PPARα) in a cell, comprising contacting the cell with an effective amount of compounds represented by formula (I)

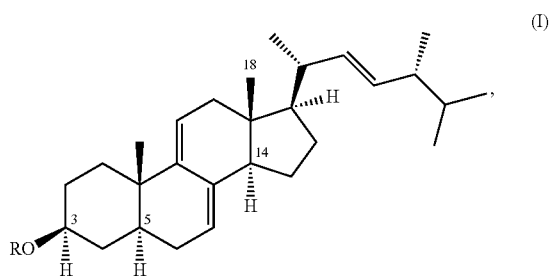

wherein R is a hydrogen atom,

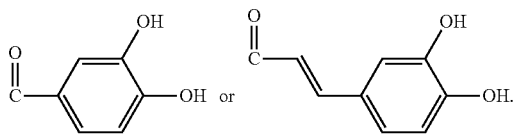 [SMILES: O=Cc1ccc(O)c(O)c1 ; O=C/C=C/c1ccc(O)c(O)c1]

Another objective of the present invention is to provide a method for increasing expression levels of membrane glucose transporter 4 (GLUT4) in skeletal muscle and phospho-AMPK in both skeletal muscle and liver tissue, comprising contacting the tissue with an effective amount of compounds represented by formula (I)

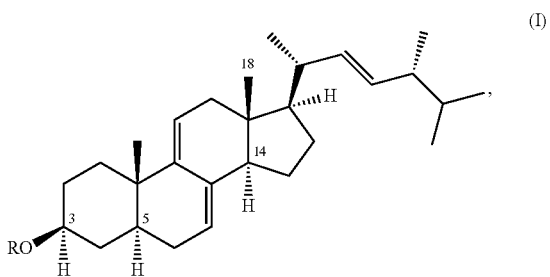

wherein R is a hydrogen atom,

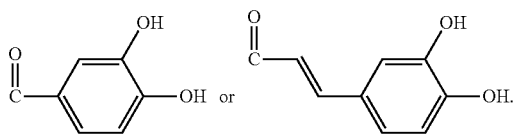 [SMILES: O=Cc1ccc(O)c(O)c1 ; O=C/C=C/c1ccc(O)c(O)c1]

According to an embodiment of the present invention, the compounds are obtained from *Antrodia camphorata*, and the compound is ergostatrien-3β-ol.

According to an embodiment of the present invention, the effective amount of the compounds given is from 10 mg/kg to 40 mg/kg per day.

According to an embodiment of the present invention, the cell or tissue is obtained from a subject with diabetes.

According to an embodiment of the present invention, the cell or tissue is obtained from a subject with a condition of hyperglycemia, hyperlipidemia, dyslipidemia or hepatic total lipids.

According to an embodiment of the present invention, the compounds treat diabetes by decreasing blood glucose and HbA1c levels, and affecting insulin concentration.

According to an embodiment of the present invention, According to an embodiment of the present invention, According to an embodiment of the present invention, the compounds increase blood HDL-C levels.

According to an embodiment of the present invention, the compounds treat hepatic fat induced by high-fat-diet to decrease hepatic total lipids and triacylglycerol levels.

According to an embodiment of the present invention, the compounds treat adipocyte and hepatic ballooning degeneration induced by high-fat-diet to reduce sizes of visceral adipocyte and hepatic ballooning degeneration.

According to an embodiment of the present invention, the compounds treat hyperleptinemia induced by high-fat-diet to reduce blood leptin levels.

According to an embodiment of the present invention, the compounds reduce visceral fat mass and hypertrophy of adipocyte induced by high-fat-diet.

The present invention provides a method for treating diabetes, hyperlipidemia or hepatic total lipids by using ergostatrien-3β-ol and its derivatives, these compounds can significantly lower the blood markers, such as blood glucose, glycated hemoglobin (HbA1c), total cholesterol (TC), triglyceride (TG), insulin, and leptin levels in subjects with type 2 diabetes, hyperlipidemia or hepatic total lipids, finally ameliorate insulin resistance. Therefore, the method of the present invention provides a new strategy to prevent and treat type 2 diabetes, hyperlipidemia or hepatic total lipids.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
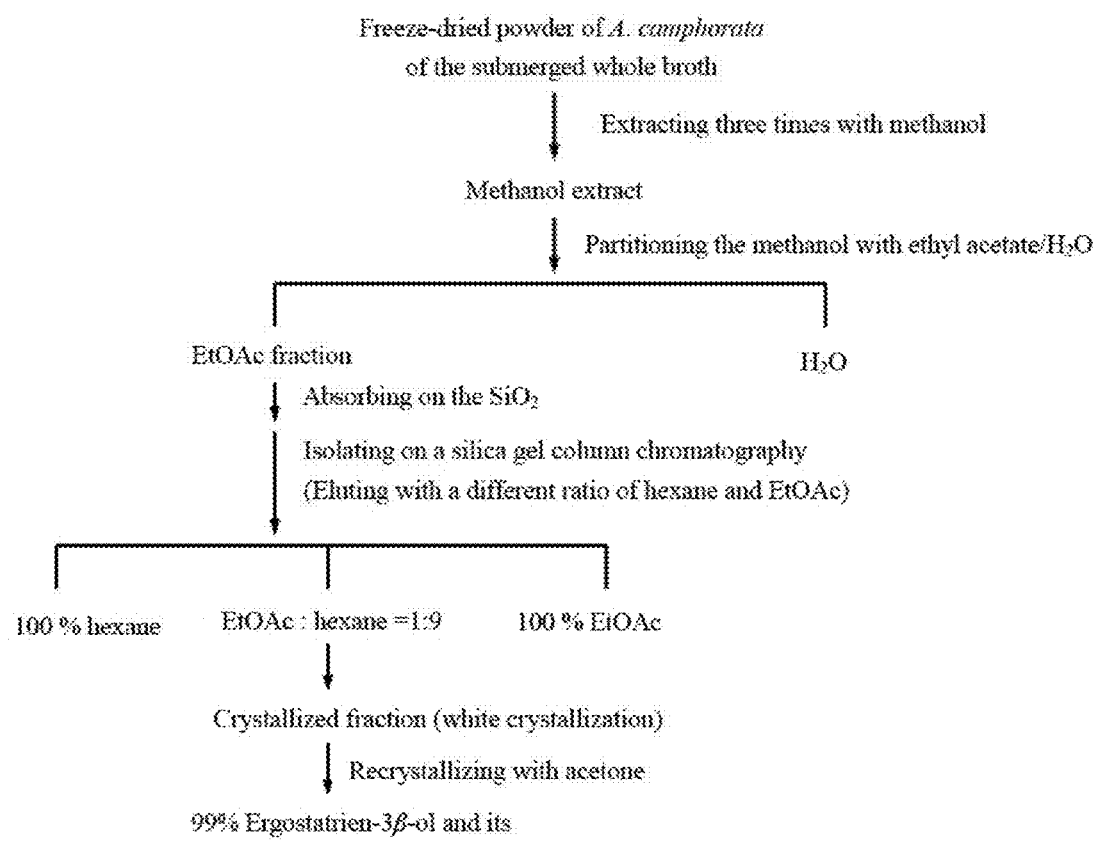
FIG. 1 shows a flowchart for the preparation of ergostatrien-3β-ol and its derivatives extracted from *Antrodia camphorata*.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

DEFINITION

The "effective amount" described in the present invention represents the amount of ergostatrien-3β-ol (ergosta-7,9(11),22-trien-3β-ol) and its derivatives obtained from *Antrodia camphorata* that can treat diabetes, hyperlipidemia or hepatic total lipids in animals and humans. The effective amount may vary depending on the organism or individual treated but can be determined experimentally using various techniques, including a dose escalation study.

As used herein, the data provided represent experimental values that can vary within a range of ±20%, preferably within ±10%, and most preferably within ±5%.

The present invention provides a method to treat diabetes, hyperlipidemia or hepatic total lipids, comprising: administering an effective amount of ergostatrien-3-ol and its derivatives obtained from *Antrodia camphorata* to a subject in need thereof. The experiments below show the effects of the ergostatrien-3β-ol on tissue weight, liver lipids and blood profiles of mice. Generally, ergostatrien-3β-ol can be given to mammals and humans at a dose of 10 mg/kg-40 mg/kg of body weight per day. The invention is described in detail below.

Statistical Analysis: all results are presented as mean and standard error. Whenever possible, data are subjected to analysis of variance, follows by Dunnett's multiple range tests, using SPSS software (SPSS Inc., Chicago, Ill., USA). $P<0.05$ is considered to be statistically significant.

The present invention provides a method for treating diabetes, hyperlipidemia or hepatic total lipids comprising administering to the subject in need thereof an effective amount of and its derivatives obtained from *Antrodia camphorata*. The experiments below show the effects of ergostatrien-3β-ol and its derivatives on blood levels of HbA1c, blood and hepatic lipid, blood leptin and insulin levels. Generally, ergostatrien-3β-ol and its derivatives can be given to mammals and humans at a dose of 10 mg/kg to 40 mg/kg of body weight per day.

In the present invention, the model of C57BL/6J mouse that is fed a high fat-diet (HFD) is a robust and efficient model for early type 2 diabetes. The C57BL/6J mouse is susceptible not only to HFD-induced marked increases in adipose tissue mass but also to pronounced insulin resistance, hyperlipidemia, hyperinsulinemia, hypertriglycemia and hypercholesterolemia. Metformin is a widely used antidiabetic agent in the treatment of type 2 diabetes mellitius. Metformin activates AMPK in both hepatocyte and skeletal muscle. Thiazolidinediones (TZDs) are a type 2 diabetes pills to help control the symptoms of diabetes, it not only activates AMPK through a signal pathway that is different from metformin but also further activate AMPK. This influence in plasma adipocytokine concentration is associated with a decrease in accumulation in the liver and improvement in insulin resistance. Thus, one of the TZDs, rosiglitazone, and an andyslipidemia drug, fenofibrate (activating AMPK), are chosen as a positive control for comparison with the antidiabetic effects of ergostatrien-3β-ol and its derivatives. Phosphorylation of Thr 172 of a subunits is essential for AMPK activity. Therefore, HFD-fed mouse models are chosen to address the effect and mode of action of ergostatrien-3β-ol and its derivatives on AMPK activity and membrane GLUT4 content, and to compare with rosiglitazone and fenofibrate. As a possible molecular mechanism of ergostatrien-3β-ol, the target gene expressions involved in antidiabetes and antihyperlipidemia in peripheral tissues are also investigated.

The present invention provides ergostatrien-3β-ol and its derivatives extracted from *A. camphorata* is used to prepare a medicament for lowering glucose levels, hepatic fat, triglyceride and treating diabetes. The invention is described in detail below to illustrate the method of preparing the *A. camphorata* extract and its effect.

EXAMPLE 1

Preparation of Ergostatrien-3/3-Ol and its Derivatives Obtained from *Antrodia camphorata*

Fungus Material: the freeze-dried powder of *Antrodia camphorata* submerged whole broth is provided by the Biotechnology Center of Grape King Inc., Chung-Li City, Taiwan.

Figure 2:
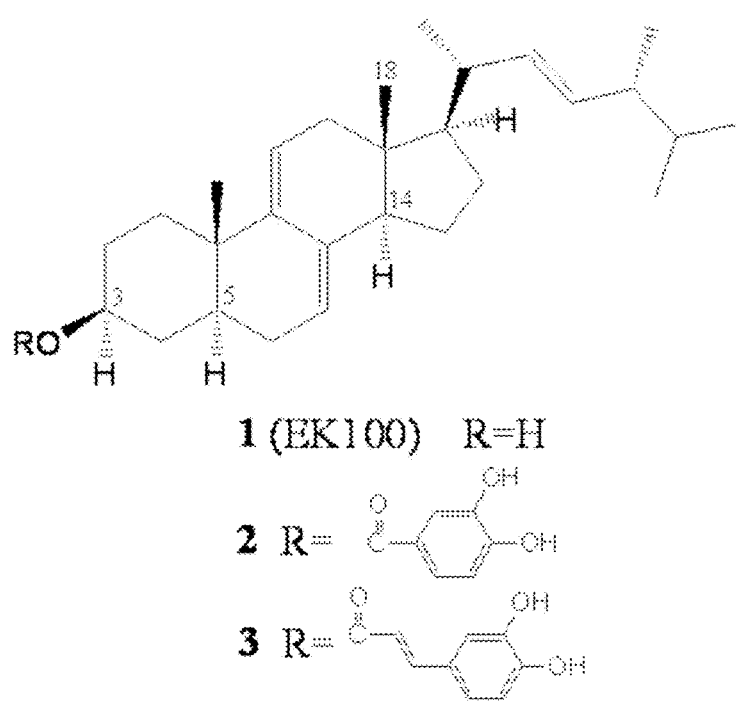
FIG. 2 shows the chemical structure of ergostatrien-3β-ol (ergosta-7,9(11), 22-trien-3β-ol) and its derivatives.

Isolation and Determination of the Active Compound: the *A. camphorata* extracts of the present invention are the single components extracted from the freeze-dried powder of *A. camphorata*. As shown in FIG. 1, the freeze-dried powder of *A. camphorata* of the submerged whole broth (1.6 kg) is extracted three times with methanol (16 L) at room temperature (1 day each). The methanol extract is evaporated in vacuo to obtain a brown residue, which is suspended in $H_2O$ (1 L) and then partitioned (three times) with 1 L of ethyl acetate (EtOAc). The EtOAc fraction (95 g) is chromatographed on silica gel and eluted with a different ratio of hexane and EtOAc (e.g. 100% hexane, EtOAc:hexane=1:9, 100% EtOAc) to increase polarity and further purified with high performance liquid chromatography (HPLC). Ergostatrien-3β-ol (ergosta-7,9(11),22-trien-3β-ol) and its derivatives (5.4 g) are eluted with 10% EtOAc in hexane, and recrystallization with acetone. As show in FIG. 2, the structure of ergostatrien-3β-ol and its derivatives are represented by formula (I)

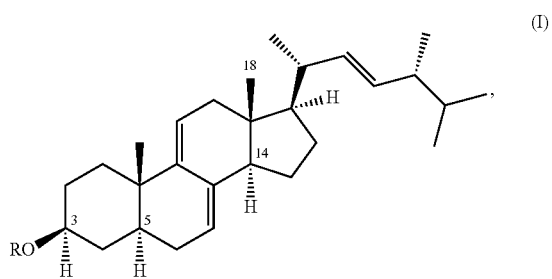

wherein R is a hydrogen atom,

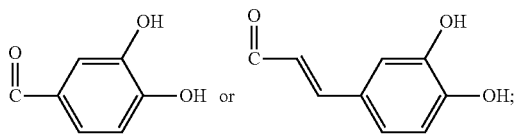 [SMILES: O=Cc1ccc(O)c(O)c1 ; O=C/C=C/c1ccc(O)c(O)c1]

and when R is a hydrogen, the compound is ergostatrien-3β-ol, when R is

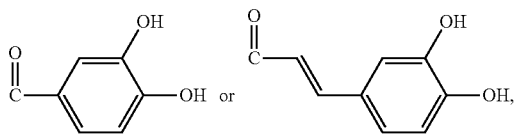 [SMILES: O=Cc1ccc(O)c(O)c1 ; O=C/C=C/c1ccc(O)c(O)c1]

the compounds are the derivatives of ergostatrien-3β-ol.

EXAMPLE 2

Effects of Ergostatrien-3β-Ol on Absolute Tissue Weight, Liver Lipids and Blood Profiles Experimental Animals: the experiments are conducted under the guidelines of the Institutional Animal Care and Use Committee of Central Taiwan University of Science and Technology. As previously described, four-week-old male C57BL/6J mice (n=63) is purchased from the National Laboratory Animal Breeding and Research Center, Ministry of Science and Technology. After 1-week of acclimatization, mice are designed to initiate the study, and the study lasts for 12 weeks. First, mice are divided randomly into two groups (the control (CON) group (n=9), which receives a low-fat diet (Diet 12450B, Research Diets, Inc., New Brunswick, N.J., USA), and the high-fat diet (HFD)-fed group (n=54), which is fed a 45% high-fat diet (Diet 12451, Research Diets, Inc.). After 8 weeks of diet induction, HFD-treated mice are further randomly subdivided into six groups (n=9 per group), receiving ergostatrien-3β-ol (10, 20, 40 mg/kg/day body wt) or two common medications to treat type 2 diabetes, fenofibrate (Feno; purchased from Sigma Chemical Co, St Louis, and administrated at a dose of 250 mg/kg/day body wt) or rosiglitazone (Rosi; 1% methylcellulose 10 mg/kg body weight, obtained from GlaxoSmithKline Product No: BRL49653 C) or vehicle (H$_2$O) by oral gavages one time per day for another 4 weeks and still on high fat diet. The CON group and high-fat control (HF) group are given with vehicle only. The low-fat diet consisted of fat 10%, whereas the high-fat diet (HFD) consisted of fat 45% (of total energy, % kcal). The compositions of the experimental diets are shown as described. At the end of the study, food is derived from the animals (from 10 p.m. to 10 a.m.). On the next day, the mice are sacrificed, and blood and tissue are collected for analysis. Livers, skeletal muscles, and white adipose tissues (WATs) (including epididymal, mesenteric and retroperitoneal WAT) are excised and weighed, and then immediately stored in a freezer at −80° C. Heparin (30 units/mL) (Sigma) is added to blood samples. Plasma samples are collected by centrifugation at 1600 g for 15 min at 4° C. within 30 min, and plasma is obtained for insulin and leptin level analysis.

Body Weight, Food Intake and Tissue Weight. Throughout the embodiment, body weight and food intake are daily recorded at the same time. Body weight gain is defined as the difference between 1 day and the next day. The pellet food is weighed and placed in a cage food container. After 24 h, the remaining food is weighed and the crumbs are collected as much as possible. Based on the difference between 1 day and the next day, the daily food intake is calculated.

Figure 3A:
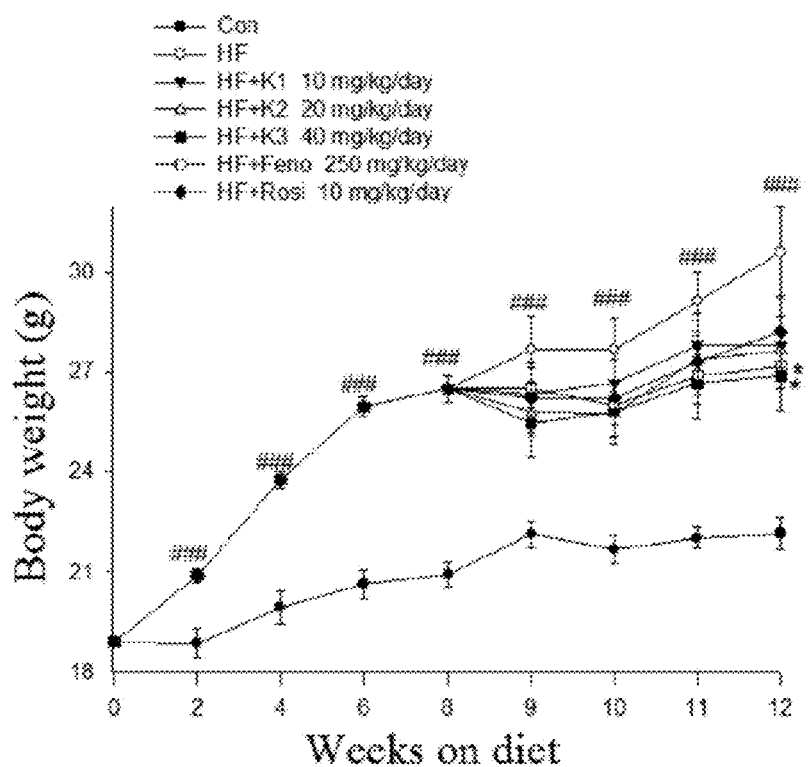
FIGS. 3A to 3H show effect of ergostatrien-3β-ol (ergosta-7,9(11), 22-trien-3β-ol) on (A) body weight, (B) food intake, (C) visceral fat, (D) blood glucose levels, (E) total cholesterol levels, (F) triglycerides levels, (G) leptin levels, and (H) insulin levels. All values are means±SE (n=9), [#] P<0.05, [##] P<0.01, and [###] P<0.001 compared with the control (CON) group; *P<0.05, P<0.01, and *P<0.001 compared with high-fat plus vehicle (HF) group by ANOVA. 10 mg/kg/day ergostatrien-3β-ol is labeled as K1; 20 mg/kg/day ergostatrien-3β-ol is labeled as K2; 40 mg/kg/day ergostatrien-3β-ol is labeled as K3; fenofibrate is labeled as Feno (250 mg/kg body wt); rosiglitazone is labeled as Rosi (10 mg/kg body wt). Visceral fat represents epididymal white adipose tissue (WAT) plus retroperitoneal WAT.
Figure 3B:
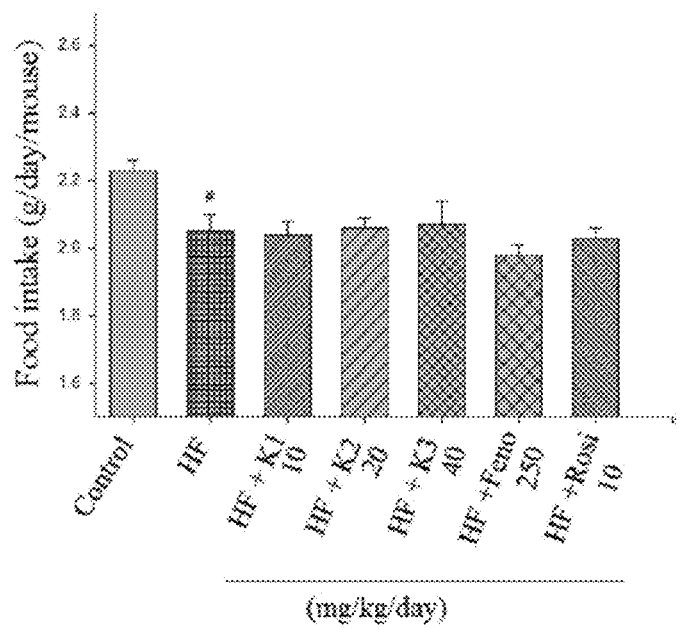
Figure 3C:
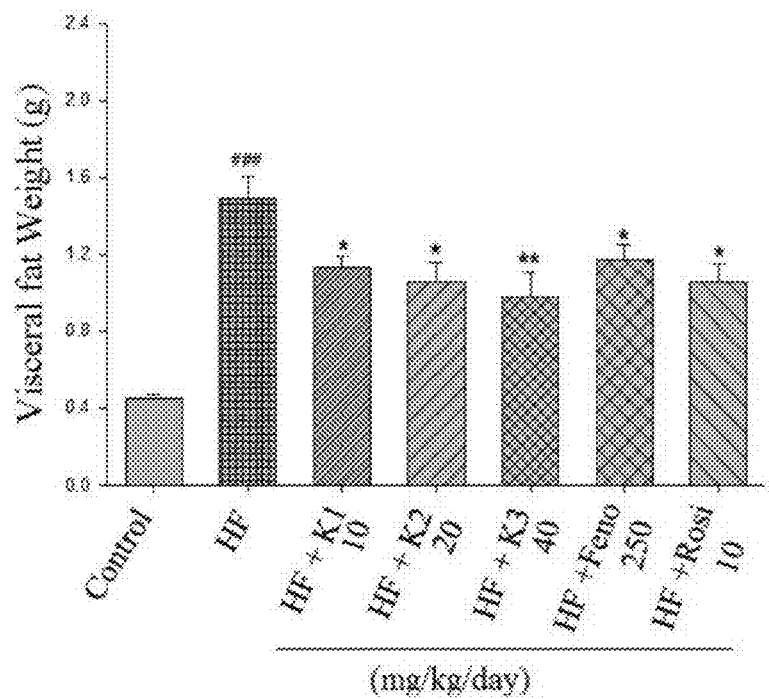

All group mice begin with similar mean body weights (18.9±0.2 g). Mice on HFD for 12 weeks displayed significantly greater increases in body weight and body weight gain compared to CON littermates (FIG. 3A and Table 1). Administration of 40 mg/kg/day ergostatrien-3β-ol (labeled as K3) and Feno displays resistance to bodyweight gain. HF mice consume high-fat diets much less than CON littermates (FIG. 3B). All the ergostatrien-3β-ol-, Feno- and Rosi-treated mice and HF mice consume high-fat diets similarly. Feeding a HFD displays a marked increase in weights of absolute adipose tissues (epididymal, visceral fat, mesenteric and retroperitoneal WAT) (Table 2 and FIG. 3C). The 10 mg/kg/day ergostatrien-3β-ol-(labeled as K1), 20 mg/kg/day ergostatrien-3β-ol- (labeled as K2), 40 mg/kg/day ergostatrien-3β-ol-(labeled as K3), Feno-, and Rosi-treated mice display a decrease in weights of retroperitoneal WAT and visceral fat. The K1-, K2-, K3-, and Rosi-treated mice reduce weights of epididymal WAT. The K3- and Rosi-treated mice display less mesenteric WAT weights. The brown adipose tissue (BAT) mass is decreased in K2-, K3- and Feno-treated mice. The K2- and K3-treated mice show an increase in skeletal muscle mass. Feno-treated mice show a marked increase in liver weight (Table 1).

Blood Glucose and HbA1c Levels. Blood samples (0.8 mL) are collected from the retro-orbital sinuses of fasting mice, and glucose level is measured by the glucose oxidase method (model 1500; Sidekick Glucose Analyzer; YSI Inc., Yellow Springs, Ohio, USA). Percent HbA1c is detected with a Hemoglobin A1c kit (BioSystems S.A., Barcelona, Spain). Plasma triglycerides (TG), total cholesterol (TC), free fatty acids (FFA), high-density lipoprotein cholesterol (HDL-C), and low density lipoprotein cholesterol (LDL-C) are determined using commercial assay kits (Triglycerides-E test, Cholesterol-E test, and FFA-C test, Wako Pure Chemical, Osaka, Japan; HDL-C-test and LDL-C-test, Roche Diagnostics GmbH, Indianapolis, USA) according to their instructions. A mouse insulin ELISA kit (Sibayagi, Gunma, Japan) and mouse leptin ELISA kit (Morinaga, Yokohama, Japan) are used to measure blood insulin and leptin levels, respectively.

Figure 3D:
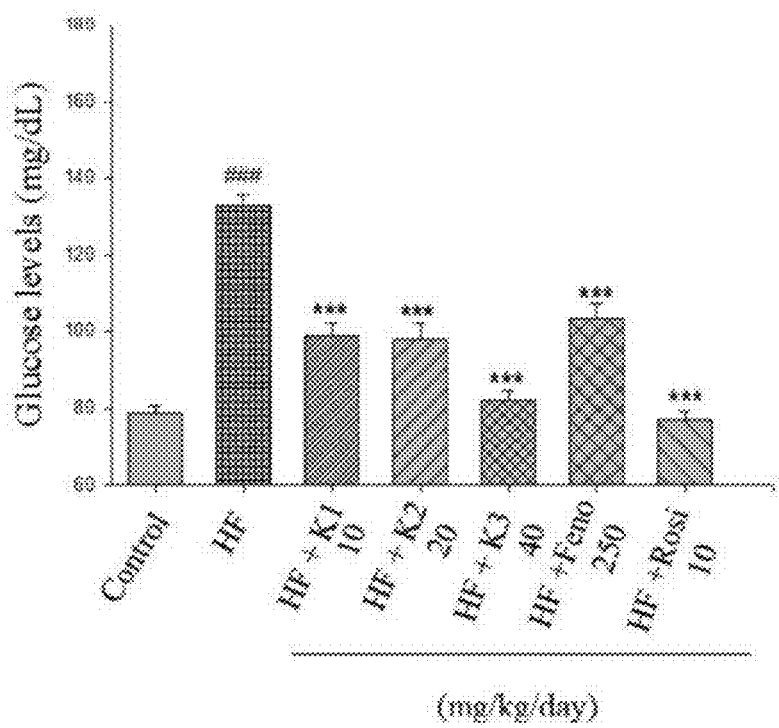
Figure 3E:
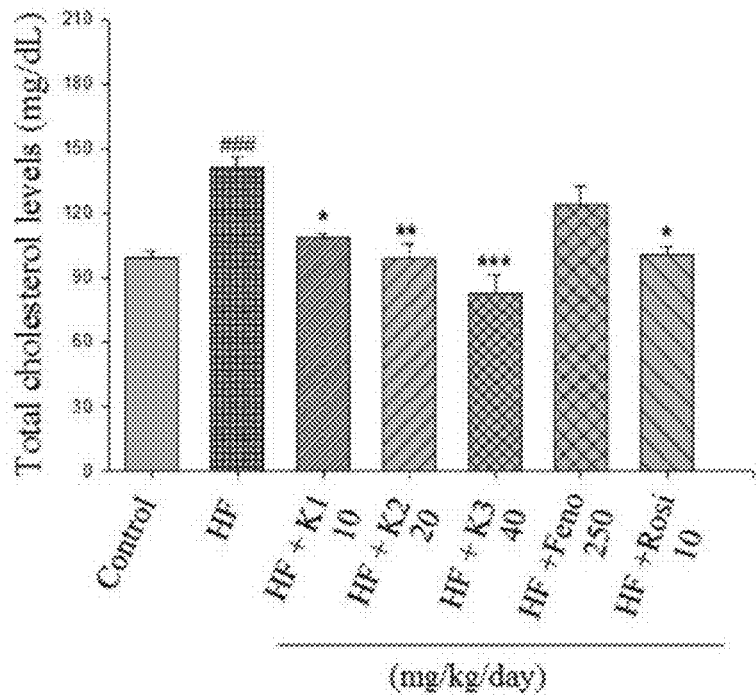
Figure 3F:
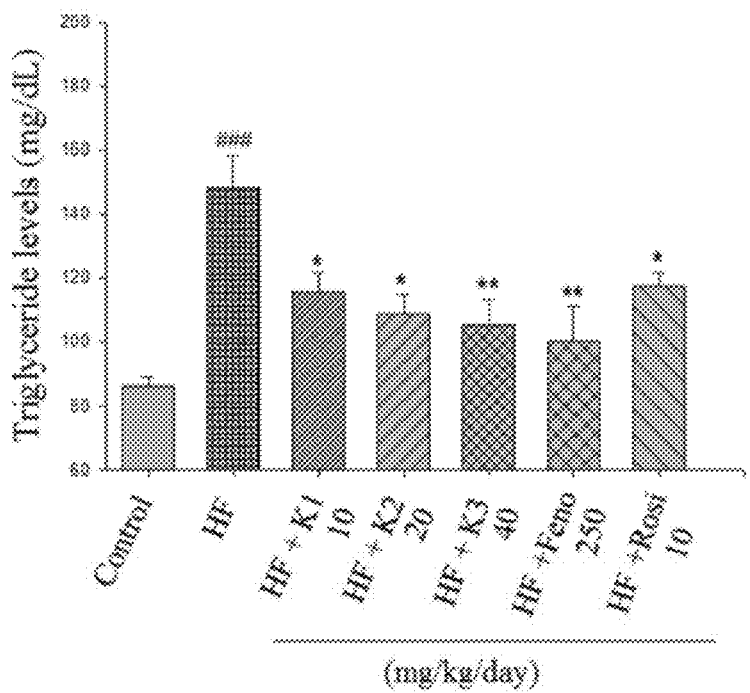
Figure 3G:
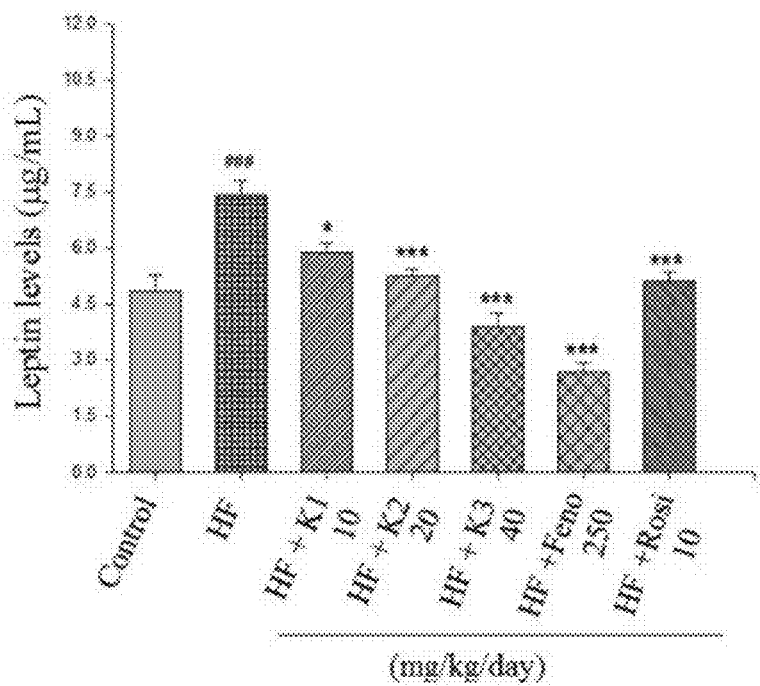
Figure 3H:
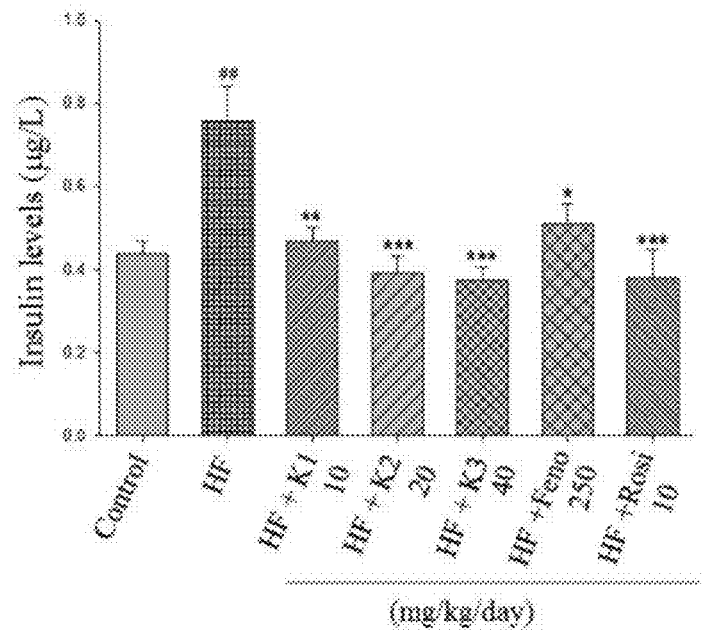

After 8 weeks on HFD, HF mice displayed the hyperglycemia evidence compares with the CON mice (P<0.001). Administration of K1, K2, K3, Feno, and Rosi significantly reduce blood glucose levels (P<0.001, P<0.001, P<0.001, P<0.001, P<0.001, respectively) (FIG. 3D). The percent of hemoglobin is evaluated nonenzymatically (percent HbA1c) as an integrated measure of long-term blood glucose regulation. Blood levels of HbA1c are significantly greater in the HF group than in the CON group. Treatment with K1, K2, K3, Feno, and Rosi decrease HbA1c levels in blood (Table 1).

Blood Lipid and Hepatic Lipid. Hepatic lipids are extracted as previously described. Liver sample (0.375 g) is homogenized with 1 mL of distilled water for 5 min for the hepatic lipid extraction and analyzed using a triglycerides kit as used for serum lipids.

HFD cause increases in blood total cholesterol (TC), triglyceride (TG), and free fatty acid (FFA) (FIGS. 2E, 2F and Table 1). The K1-, K2-, K3-, and Rosi-treated mice lower TC levels (P<0.05, P<0.01, P<0.001, P<0.05, respectively). The K1-, K2-, K3-, Feno-, and Rosi-treated mice decrease TG level. The K1-, K2-, K3-, Feno-, and Rosi-treated mice show decreased FFA concentrations. The K1-, K2-, K3-, and Feno-treated mice increase high-density lipoprotein cholesterol (HDL-C) levels (Table 1). The K3- and Rosi-treated mice display a decrease in low-density lipoprotein cholesterol (LDL-C) level. HFD cause increases in the total lipids of liver and concentrations of triacylglycerol, while treatment with K1, K2, K3, Rosi, and Feno displays marked decreases in these phenomena (Table 1).

Blood leptin and insulin levels are greater in the HF group than in the CON group (FIGS. 2G and 2H). The K1-, K2-, K3-, Feno-, and Rosi-treated mice display a decrease in blood leptin and insulin levels.

These results show that ergostatrien-3β-ol-treated mice display decreased in weights of retroperitoneal, epididymal or mesenteric WAT and visceral fat, lowered blood glucose levels accompanied by decreased HbA1c and ameliorated insulin resistance, diminished blood TC and TG levels. Ergostatrien-3β-ol derivatives also show the effect.

ergostatrien-3β-ol. The appearance of adipocyte is polyhedral and displayed the string-like cytosol surrounded by a vacuole (H&E stain); and (B) liver tissue (magnification: 10 (ocular)×20 (object lens)) from mice fed with ergostatrien-3β-ol. The high-fat diet induced the hepatic ballooning degeneration in the high-fat (HF) group as compared with the low-fat (CON) group. The ballooning degeneration is a form of liver parenchymal cell death, and the nucleolus is squeezed into the other side of the named balloon (as the arrow indicates). Each presented image is typical and representative of nine mice.

Figure 4A:
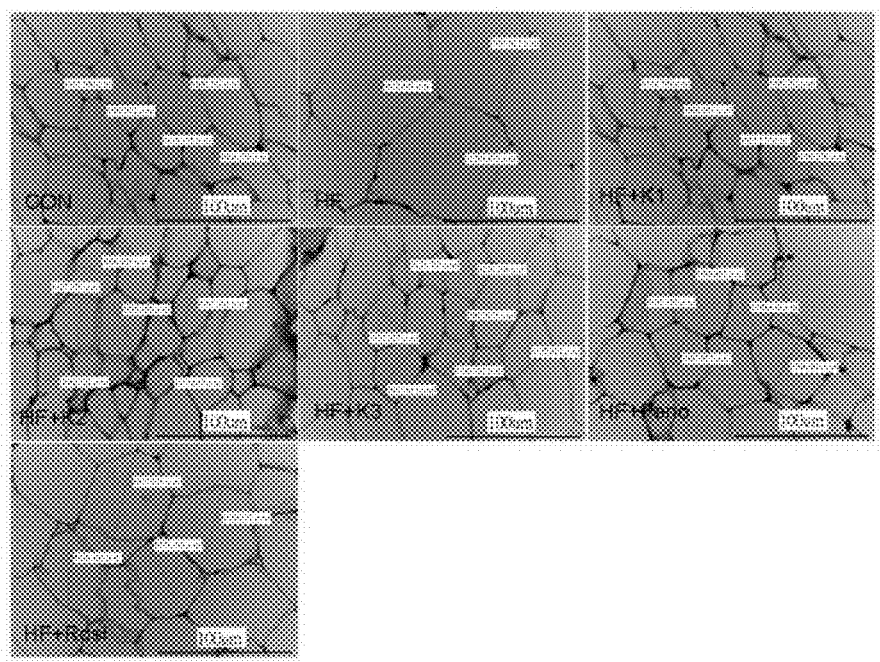
FIGS. 4A and 4B show effects of ergostatrien-3β-ol on (A) epididymal WAT and (B) liver tissue morphology in the low-fat (CON), high-fat (HF), 10 mg/kg/day ergostatrien-3β-ol (HF+K1), 20 mg/kg/day ergostatrien-3β-ol (HF+K2), 40 mg/kg/day ergostatrien-3β-ol (HF+K3); fenofibrate (Feno): HF+Feno, rosiglitazone (Rosi): HF+Rosi.

Feeding a HFD induce hypertrophy of adipocytes (the average areas of adipocytes in the HF group and CON group are 9604.2±281.3 and 3797.5±412.9 μm2, respectively), whereas mice treated with K1 (4204.0±131.5 μm2), K2 (3535.7±340.2 μm2), K3 (3458.9±30.7 μm2), and Feno (4175.4±322.9 μm2) shows significantly lower hypertrophy. The average area of the Rosi treated mice is 5598.6±162.7 μm2 (FIG. 4A). Feeding a HFD induces ballooning degen-

TABLE 1

Absolute tissue weights, liver lipid, blood HbA1c, and other parameters in HFD-mice treated orally with ergostatrien-3β-ol

| Parameter | CON | HF | HF + K1 $10^b$ | HF + K2 $20^b$ | HF + K3 $40^b$ | HF + Feno $250^b$ | HF + Rosi $10^b$ |
|---|---|---|---|---|---|---|---|
| Absolute Tissue Weight (g) | | | | | | | |
| EWAT | 0.391 ± 0.016 | 1.103 ± 0.092### | 0.853 ± 0.031* | 0.774 ± 0.057* | 0.736 ± 0.070* | 0.924 ± 0.069 | 0.813 ± 0.069* |
| MWAT | 0.197 ± 0.015 | 0.341 ± 0.032### | 0.276 ± 0.032 | 0.276 ± 0.032 | 0.244 ± 0.024* | 0.295 ± 0.009 | 0.257 ± 0.019* |
| RWAT | 0.061 ± 0.006 | 0.391 ± 0.041### | 0.281 ± 0.016* | 0.283 ± 0.025* | 0.243 ± 0.041* | 0.249 ± 0.028* | 0.244 ± 0.042* |
| Skeletal muscle | 0.462 ± 0.021 | 0.744 ± 0.051 | 0.781 ± 0.034 | 1.167 ± 0.045* | 1.351 ± 0.153*** | 0.569 ± 0.069 | 0.737 ± 0.094 |
| BAT | 0.123 ± 0.009 | 0.190 ± 0.010## | 0.160 ± 0.007 | 0.143 ± 0.016* | 0.144 ± 0.013* | 0.142 ± 0.012* | 0.175 ± 0.018 |
| Liver (g) | 0.827 ± 0.017 | 0.839 ± 0.025 | 0.813 ± 0.025 | 0.819 ± 0.025 | 0.796 ± 0.041 | 1.046 ± 0.033*** | 0.816 ± 0.038 |
| weight gain (g) | 1.21 ± 0.23 | 3.96 ± 1.24# | 1.30 ± 0.39 | 1.13 ± 0.20 | 0.37 ± 0.38* | 0.69 ± 0.63* | 1.71 ± 0.56 |
| Liver Lipids | | | | | | | |
| total lipid (mg/g) | 57.6 ± 2.8 | 97.2 ± 6.0### | 72.4 ± 3.7** | 68.0 ± 4.5** | 65.4 ± 4.2** | 63.8 ± 4.7** | 65.1 ± 5.3** |
| triacylglycerol (μmol/g) | 35.6 ± 3.7 | 80.3 ± 7.3### | 57.3 ± 5.5** | 44.5 ± 4.7*** | 43.7 ± 6.6*** | 48.4 ± 5.6*** | 44.5 ± 3.2*** |
| Blood Profiles | | | | | | | |
| FFA (meq/L) | 0.99 ± 0.09 | 1.35 ± 0.11## | 1.06 ± 0.10* | 1.05 ± 0.09* | 1.03 ± 0.05** | 0.94 ± 0.08** | 1.00 ± 0.09* |
| HbA1c (%) | 5.5 ± 0.6 | 9.3 ± 0.5### | 5.8 ± 0.7** | 5.7 ± 0.5** | 5.1 ± 0.3*** | 6.4 ± 0.7** | 6.2 ± 0.4** |
| HDL-C (mg/dL) | 84.9 ± 3.9 | 65.3 ± 3.1### | 82.2 ± 3.9** | 83.0 ± 2.0*** | 83.8 ± 1.6*** | 80.3 ± 4.5** | 73.1 ± 5.8 |
| LDL-C (mg/dL) | 107.1 ± 7.7 | 130.5 ± 20.0 | 112.4.0 ± 7.4 | 103.7 ± 10.8 | 86.8 ± 11.5** | 105.8 ± 10.4 | 86.7 ± 7.7** |

$^a$All values are means ± SE (n = 9).
P < 0.05, ##P < 0.01, and ###P < 0.001 compared with the control (CON) group;
*P < 0.05, P < 0.01, and *P < 0.001 compared with the high-fat plus vehicle (distilled water) (HF) group.
Ergostatrien-3β-ol (EK100): K1: 10, K2: 20, K3: 40 mg/kg body wt;
Feno: fenofibrate (250 mg/kg body wt);
Rosi: rosiglitazone (10 mg/kg body wt).
BAT, brown adipose tissue;
RWAT, retroperioneal white adipose tissue;
MWAT, mesenteric white adipose tissue;
FFA, plasm free fatty acid.
$^b$Dose (mg/kg/day)

EXAMPLE 3

Histopathology Examination

A portion of the collected epididymal WAT and liver tissue is fixed with formalin (200 g/kg) neutral buffered solution and embedded in paraffin. Sections (8 μm) are cut and stained with hematoxylin and eosin. A microscope (Leica, DM2500) and Leica Digital camera (DFC-425-C) are used for microscopic examination and images taken, respectively.

Figure 4B:
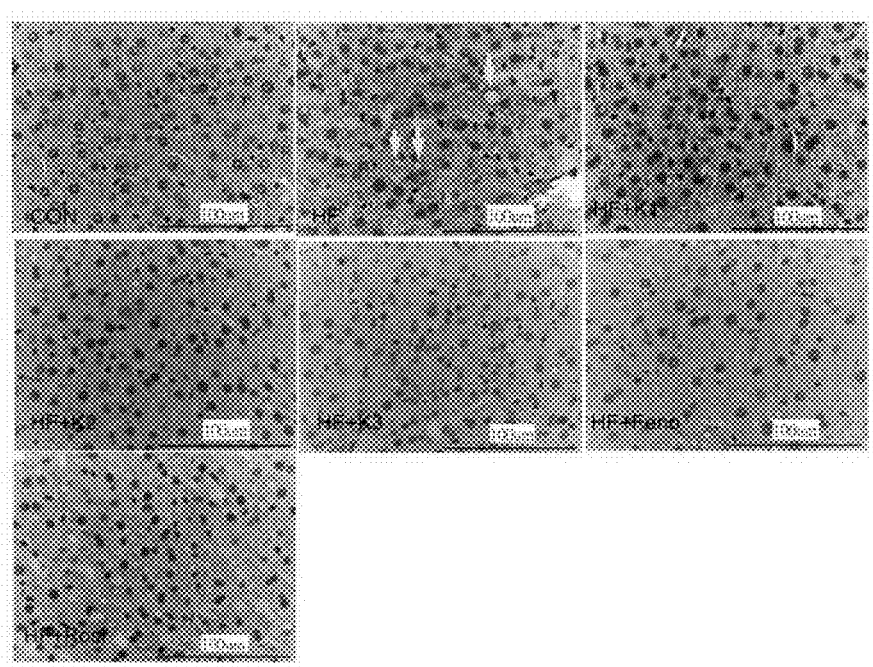
Figure 5A:
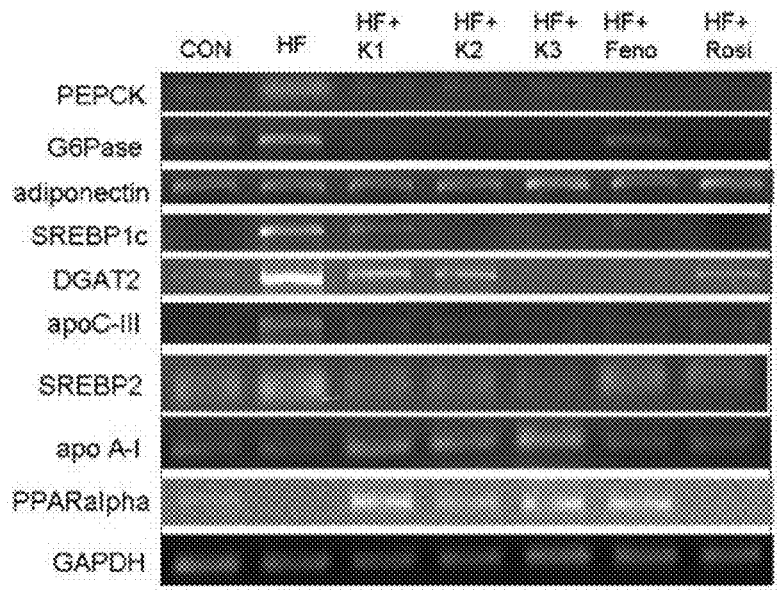
FIGS. 5A to 5D show semiquantitative RT-PCR analysis on PEPCK, G6 Pase, adiponectin, SREBP1c, DGAT2, apo SREBP2, apo A-I, and PPARα mRNA expression in liver tissue of the mice receiving ergostatrien-3β-ol (EK100). All values are means±SE (n=9). [#] P<0.05 and [###] P<0.001 compared with the control (CON) group; * P<0.05,  P<0.01, and * P<0.001 compared with the high-fat plus vehicle (HF) group. 10 mg/kg/day ergostatrien-3β-ol is labeled as K1; 20 mg/kg/day ergostatrien-3β-ol is labeled as K2; 40 mg/kg/day ergostatrien-3β-ol- is labeled as K3; fenofibrate is labeled as Feno (250 mg/kg body wt); rosiglitazone is labeled as Rosi (10 mg/kg body wt).
Figure 5B:
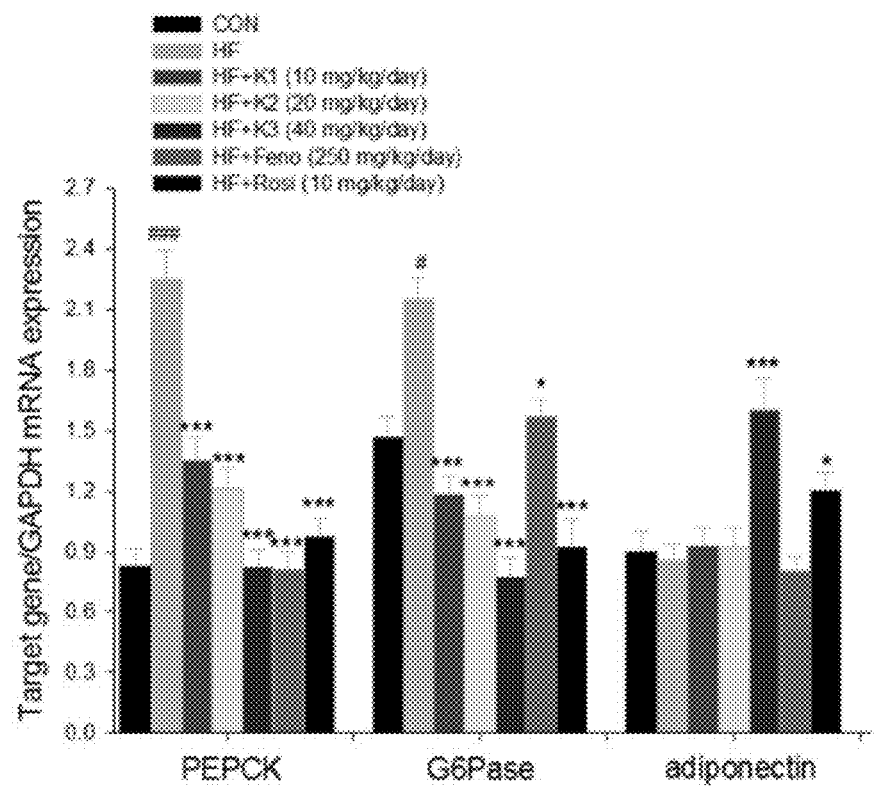
Figure 5C:
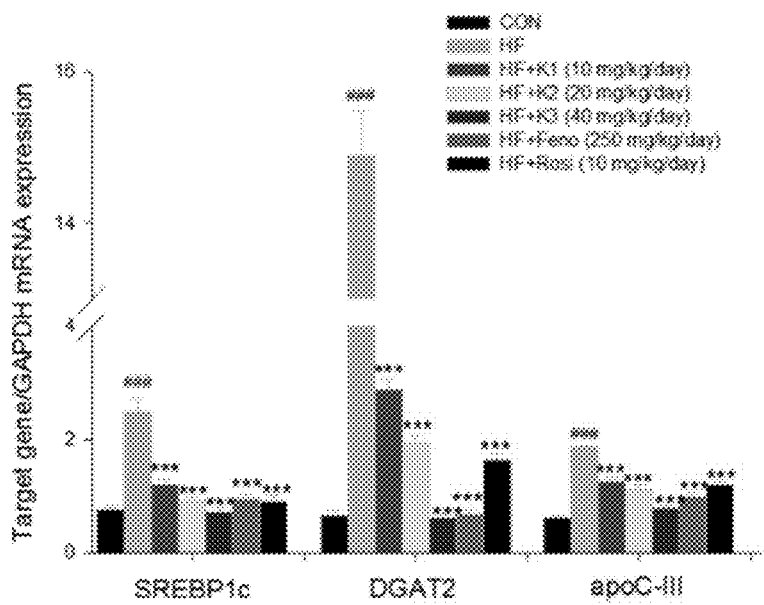
Figure 5D:
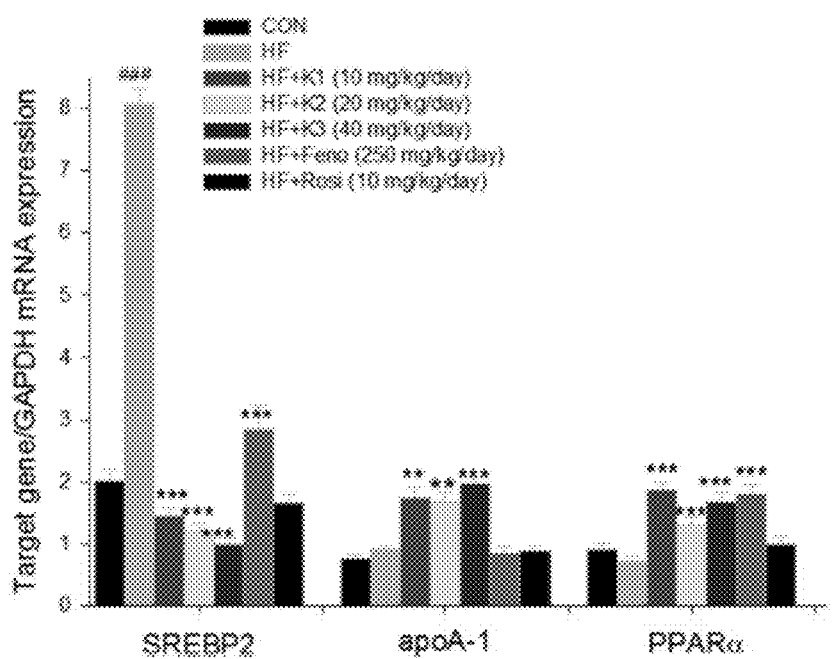

FIGS. 3A and 3B show the pictures of hematoxylin and eosin-stained sections of (A) epididymal adipocytes (magnification: 10 (ocular)×20 (object lens)) from mice fed with eration of hepatocyte. Administration of K1, K2, K3, Feno, and Rosi decreases the ballooning degeneration (FIG. 4B). These results indicate that ergostatrien-3β-ol can lower hypertrophy of adipocytes and decrease liver parenchymal cell death. Ergostatrien-3β-ol derivatives also show the effect.

EXAMPLE 4

Targeted mRNA Levels and Gene Expressions in Liver Tissue

There are several genes regulate type 2 diabetes associated with hyperlipidemia: membrane glucose transporter resistance (GLUT4), phosphoenol pyruvate carboxykinase (PEPCK), glucose-6-phosphatase (G6 Pase), sterol regulatory element binding protein 1c (SREBP1c), SREBP2, apolipoprotein A-I (apo A-D, peroxisome proliferator activated receptor α (PPARα), diacylglycerol acyltransferase 2 (DGAT2) and AMP-activated protein kinase (AMPK).

Membrane glucose transporter 4 (GLUT4) is a key regulator of whole body glucose homeostasis. Both insulin and exercise induce a translocation of membrane GLUT4 from intracellular storage compartments toward the plasma membrane in adipocytes and skeletal muscle cells, allowing the cell to take up glucose. Impairment of membrane GLUT4 expressions, membrane GLUT4 translocation, and/or insulin signaling may affect insulin stimulated glucose uptake, which would result in insulin resistance and hyperglycemia. Thus, therapeutic strategies based on enhancing membrane GLUT4 expressions may facilitate drug discovery.

AMP-activated protein kinase (AMPK) is a key regulator of glucose and lipid metabolism. Because glucose and lipid metabolism is dysregulated in type 2 diabetes mellitus, AMPK modulators have been proposed to be promising therapies. Metformin is also known to activate AMPK and stimulate human skeletal muscle, promote GLUT4 membrane translocation, and stimulate insulin-independent glucose uptake.

Thiazolidinediones (TZDs) such as rosiglitazone are antidiabetic peroxisome proliferator-activated receptor (PPAR)γ agonists. PPARγ activator like TZDs decreases blood glucose levels. Rosiglitazone does not stimulate insulin secretion. Rosiglitazone is approved for glycemic control in people with type 2 diabetes. Rosiglitazone directly targets insulin resistance and increases peripheral glucose uptake, thus improving glycemic control. The modes of action of rosiglitazone mainly contributed to the insulin-sensitizing effect and membrane GLUT4 levels.

Fenofibrate is an activator of PPARα and has been used for the management of hypertriglyceridemia for many years. PPARα is a key regulator of genes associated with lipid metabolism, which results in a decrease in circulating triglycerides and fatty acids via modulation of many target genes involved in lipogenesis, fatty acid oxidation, and energy expenditure.

The experiment is performed as in a previously described protocol. Total RNA from the liver tissue is isolated with a Trizol reagent (Molecular Research Center, Inc., Cincinnati, Ohio, USA) according to the manufacturer's directions. Total RNA (1 μg) is reverse transcribed to cDNA with 5 μL of Moloney murine leukemia virus reverse transcriptase (Epicenter, Madison, Wis., USA) as a previously described protocol. The polymerase chain reaction (PCR) is performed in a final 25 μL containing 1 U Blend Taq-Plus (TOYOBO, Japan), 1 μL of the RT first-strand cDNA product, 10 μM of each forward (F) and reverse (R) primer, 75 mM Tris-HCl (pH 8.3) containing 1 mg/L Tween 20, 2.5 mM dNTP, and 2 mM $MgCl_2$. The primers are shown in Table 2. The products are run on 2% agarose gels and stained with ethidium bromide. The relative density of the band is evaluated using AlphaDigiDoc 1201 software (Alpha Innotech Co., San Leandro, Calif., USA). All of the measured PCR products are normalized to the amount of cDNA of GAPDH in each sample.

TABLE 2

Primers Used in This Study

| Gene | SEQ ID NO. | Primer sequence | PCR product (bp) | Annealing temp (° C.) |
|---|---|---|---|---|
| PEPCK | 1<br>2 | F: CTACAACTTCGGCAAATACC<br>R: TCCAGATACCTGTCGATCTC<br>(Seq No. NM_011044.2) | 330 | 52 |
| G6 Pase | 3<br>4 | F: GAACAACTAAAGCCTCTGAAAC<br>R: TTGCTCGATACATAAAACACTC<br>(Seq No. NM_008061.3) | 350 | 50 |
| Adiponectin | 5<br>6 | F: TCTTCTACAACCAACAGAATCA<br>R: GTATCATGGTAGAGAAGGAAGC<br>(Seq No. NM_009605.4) | 324 | 50.5 |
| PPARα | 7<br>8 | F: ACCTCTGTTCATGTCAGACC<br>R: ATAACCACAGACCAACCAAG<br>(Seq No. NM_011144) | 352 | 55 |
| SREBP1c | 9<br>10 | F: GGCTGTTGTCTACCATAAGC<br>R: AGGAAGAAACGTGTCAAGAA<br>(Seq No. NM_011480) | 219 | 50 |
| DGAT2 | 11<br>12 | F: AGTGGCAATGCTATCATCATCGT<br>R: AAGGAATAAGTGGGAACCAGATCA<br>(Seq No. NM_026384.3) | 149 | 50 |
| apo C-III | 13<br>14 | F: CAGTTTTATCCCTAGAAGCA<br>R: TCTCACGACTCAATAGCTG<br>(Seq No. NM_023114.3) | 349 | 47 |
| SREBP2 | 15<br>16 | F: ATATCATTGAAAAGCGCTAC<br>R: ATTTTCAAGTCCACATCACT<br>(Seq No. AF289715.2) | 256 | 47 |
| apo A-I | 17<br>18 | F: ACATATATAGACCAGGGAAGAA<br>R: AAACTGGGACACATAGTCTCT<br>(Seq No. NM_009692.3) | 246 | 50.5 |

TABLE 2-continued

Primers Used in This Study

| Gene | SEQ ID NO. | Primer sequence | PCR product (bp) | Annealing temp (° C.) |
|---|---|---|---|---|
| GAPDH | 19 20 | F: TGTGTCCGTCGTGGATCTGA R: CCTGCTTCACCACCTTCTTGA (Seq No. NM_031144) | 99 | 55 |

The HFD induces higher expression levels of phosphoenol pyruvate carboxykinase (PEPCK), glucose-6-phosphatase (G6 Pase), sterol regulatory element binding protein 1c (SREBP1c), acylcoenzyme A: diacylglycerol acyltransferase 2 (DGAT2), apolipoprotein C-III (apo C-III), and SREBP2 in the HF group than in the CON group. Administration of K1, K2, K3, Feno, and Rosi show a decreased mRNA level of PEPCK, G6 Pase, SREBP1c, DGAT2, apo C-III, and SREBP2. K3- and Rosi-treated mice increase the mRNA level of adiponectin. The K1-, K2-, and K3-treated mice show increased mRNA levels of apolipoprotein A-I (apo A-I). Administration of K1, K2, K3, and Feno increase the mRNA level of PPARα (FIGS. 5A to 5D).

EXAMPLE 5

Western Blotting of GLUT4, Phospho-Akt (Ser 473)/Total Akt, and Phospho-AMPK (Thr172) Protein Protein extractions and immunoblots for the determination of membrane GLUT4, phospho-AMPK (Thr172), and phospho-Akt (Ser 473) proteins are carried out on frozen skeletal muscle and liver tissue from mice, which follows a previous paper. Additionally, membrane GLUT4 is carried out on frozen skeletal muscle from mice, and the total membrane fractions are collected with buffer and centrifuged as a previously described. The protein contents of membrane GLUT4, phospho-AMPK, phospho-Akt, total AMPK, and total Akt are detected by western blotting. Western blotting has been determined as described elsewhere. Subsequently, antibodies are detected using horseradish peroxidase linked to a goat anti-IgG rabbit secondary antibody and visualized using an ECL system. Membrane GLUT4, structural proteins GAPDH and β-actin are purchased from Santa Cruz Biotechnology (Santa Cruz, Calif., USA); phospho-AMPK was obtained from Abcam Inc. (Cambridge, Mass., USA); phospho-Akt, total AMPK, and total Akt are from Cell Signaling Technology, Inc. (Danver Mass., USA); the BCA protein assay kit is from Thermo Scientific (Rockford, Ill., USA); and the ECL reagent kit is from GE Healthcare BioSciences (Buckinghamshire, UK). The secondary antibody antirabbit is from Jackson ImmunoResearch Laboratories, Inc. (West Grove, Pa., USA). The density blotting is analyzed using Alpha Easy FC software (Alpha Innotech Corp., Randburg, South Africa). Structural proteins GAPDH and β-actin are obtained by stripping the nitrocellulose membrane proteins of liver and skeletal muscle, respectively.

Figure 6A:
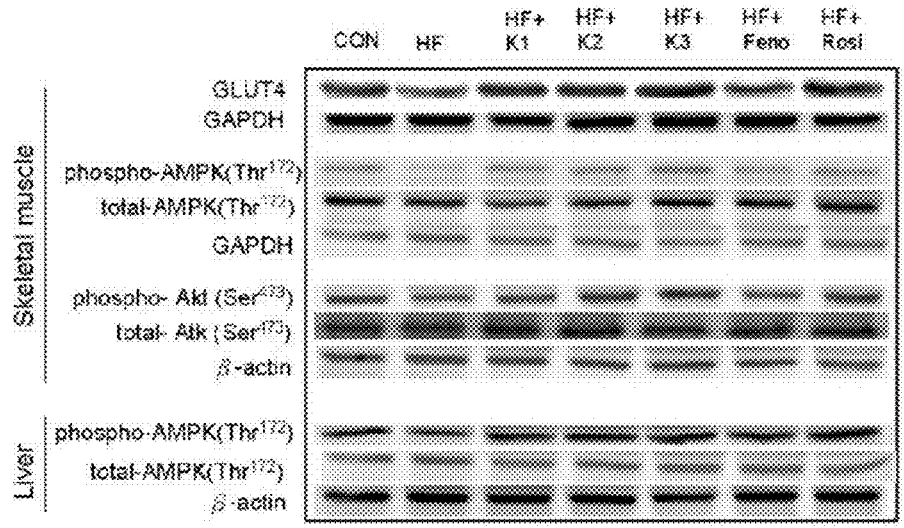
FIGS. 6A and 6B show protein contents of membrane glucose transporter 4 (GLUT4), phospho-AMPK (Thr 172)/total AMPK in liver tissue of mice receiving ergostatrien-3β-ol. Protein is separated by 12% SDS-PAGE detected by Western blot. All values are means±SE (n=9). [#] P<0.05 and [###] P<0.001 compare with the control (CON) group; * P<0.05,  P<0.01, and * P<0.001 compare with the high-fat plus vehicle (HF) group. 10 mg/kg/day ergostatrien- 3β-ol is labeled as K1; 20 mg/kg/day ergostatrien-3β-ol is labeled as K2; 40 mg/kg/day ergostatrien-3β-ol- is labeled as K3; fenofibrate is labeled as Feno (250 mg/kg body wt); rosiglitazone is labeled as Rosi (10 mg/kg body wt).
Figure 6B:
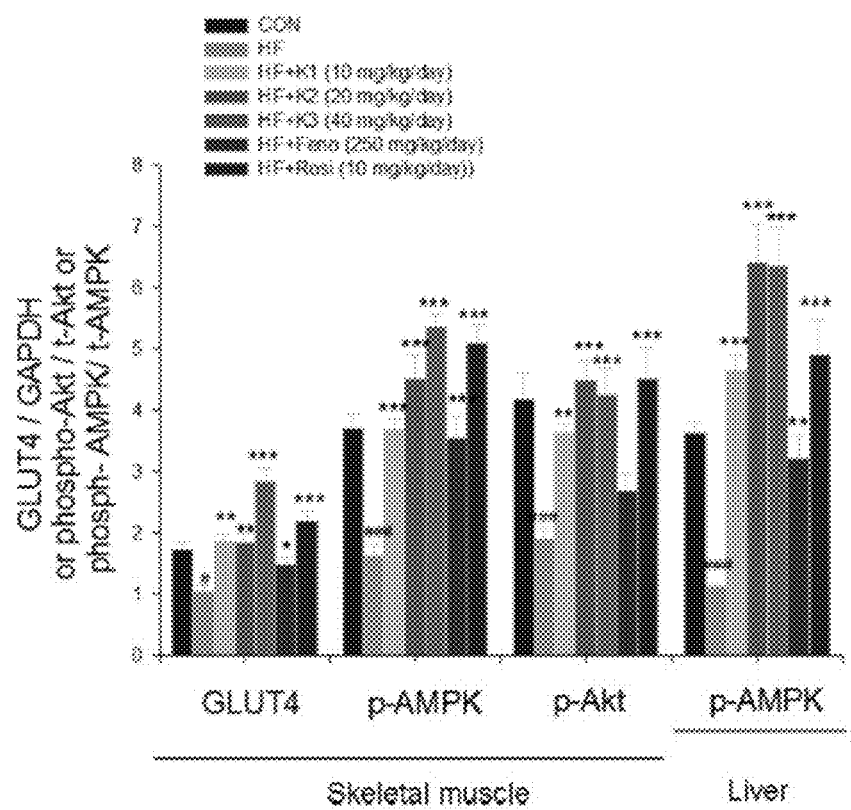

The levels of membrane GLUT4 and phospho-Akt/total Akt are lower in HF mice than in CON mice. K1-, K2-, K3-, Feno-, and Rosi-treated mice show increased muscular membrane GLUT4 protein contents ($P<0.01$, $P<0.01$, $P<0.001$, $P<0.05$, $P<0.001$, respectively). Administration of K1, K2, K3, and Rosi displays higher levels of phospho-Akt/total Akt than in HF mice. The mice on HFD show decreased phospho-AMPK in liver tissue and skeletal muscle. The protein contents of phospho-AMPK are significantly increased in the K1-, K2-, K3-, Feno-, and Rosi-treated groups in liver tissue ($P<0.001$, $P<0.001$, $P<0.001$, $P<0.01$, $P<0.001$, respectively) and in skeletal muscle ($P<0.001$, $P<0.001$, $P<0.001$, $P<0.001$, $P<0.001$, respectively) (FIGS. 6A and 6B).

These all results demonstrate that ergostatrien-3β-ol-treated mice display effectively lower blood glucose and circulating triglyceride levels. In present invention, high-fat feeding induces hyperglycemia and hyperinsulinemia. Ergostatrien-3β-ol treatment significantly decreases blood glucose levels and makes mice resistant to HFD-induced hyperinsulinemia, suggesting ergostatrien-3β-ol displays increased insulin sensitivity or efficiency. In present invention, rosiglitazone and fenofibrate cause reduced blood glucose level, consistent with earlier observations. Moreover, the level of blood glycosylated HbA1c, which is a maker of long term control of blood glucose, is also significantly decreased. On the other hand, HFD causes an increase in circulating triglyceride and total cholesterol levels, which are consistent with earlier studies, while they are significantly lowered in ergostatrien-3β-ol-treated mice. These results reinforce that ergostatrien-3β-ol is effective to improve insulin resistance and dyslipidemia in a mouse model of Type 2 diabetes and dyslipidemia. The physiological relevance of these findings is supported by the increased skeletal muscular membrane GLUT4 contents and activation of AMPK in both skeletal muscle and liver tissue.

To ascertain whether ergostatrien-3β-ol regulates glucose utilization, the present invention evaluates the membrane protein contents of membrane GLUT4 in skeletal muscle because glucose uptake is primarily mediated by skeletal muscle. Levels of membrane GLUT4 movement to the plasma membrane are assessed, as it is an essential step for insulin-responsive glucose in skeletal muscle that becomes defective in insulin resistance. All ergostatrien-3β-ol-treated mice display an enhancement of muscular membrane GLUT4 protein; moreover, 40 mg/kg/day ergostatrien-3β-ol and rosiglitazone treatment display approximately 2.7-fold and 2.1-fold enhancement, respectively, implying that ergostatrien-3β-ol treated mice are indeed hypersensitive to insulin and exhibit antidiabetic activity. Rosiglitazone has been shown to act as an insulin sensitizer.

The apparent insulin sensitivity of ergostatrien-3β-ol-treated mice prompts our interest in ergostatrien-3β-ol regulation of membrane GLUT4 and Akt. There are two principal mechanisms involved in promoting translocation of membrane GLUT4 to the plasma membrane, including insulin signaling through the phosphatidylinositol 3' kinase (PI3-kinase)/Akt pathway and the AMPK pathway. Previous findings show that a mutation in the gene encoding Akt2/PK Bβ results in severe insulin resistance, establishing Akt2/PKBβ as a key protein in the maintenance of euglycemia. To explore the mechanism of enhanced membrane GLUT4 proteins by ergostatrien-3β-ol, phosphorylation of Akt levels in skeletal muscle is measured. Ergostatrien-3β-ol manifests elevated phosphorylation of Akt levels in skeletal muscle, implying that the enhanced membrane GLUT4 proteins by ergostatrien-3β-ol appear to be in part mediated by the insulin signaling pathway through increased phosphorylation of Akt.

The phosphorylation of the AMPK pathway is another major regulator of membrane GLUT4 translocation during exercise or in response to some antidiabetic agents such as 5-Aminoimidazole-4-carboxamide ribonucleotide (AICAR) and metformin. In this present invention, ergostatrien-3β-ol-treated mice manifest elevated phosphorylation of AMPK levels in both skeletal muscle and liver tissue. Metformin is used for the treatment of type 2 diabetes due to increased skeletal muscular glucose uptake and reduced hepatic glucose production. The present results demonstrate that ergostatrien-3β-ol-treated mice are protected from HFD-induced hyperglycemia by enhancement of activation of AMPK and membrane GLUT4 proteins.

PEPCK and G6 Pase are key rate-limiting enzymes of gluconeogenesis. The liver of diabetic rats shows a significant increase in the activities of G6 Pase. Overexpression of PEPCK enzyme in mice results in symptoms of type 2 diabetes. Activation of AMPK in turn inhibits the expression of the hepatic gluconeogenic genes PEPCK and G6 Pase, activation of AMPK has been implicated in metformin action in hepatocytes. Metformin decreases hyperglycemia primarily by suppressing glucose production by the liver (hepatic gluconeogenesis). Ergostatrien-3β-ol-treated mice elicit decreased expressions of PEPCK and G6 Pase. Thus, the antidiabetic effect of ergostatrien-3β-ol is possibly partly due to down-regulation of PEPCK and G6 Pase. Collectively, this present invention demonstrates that ergostatrien-3β-ol causes glucose lowering by AMPK activation in both liver tissue and skeletal muscle, besides its ability to increase glucose uptake in skeletal muscle, possibly by down-regulations of PEPCK to inhibit hepatic glucose production.

Additionally, the present invention also validates the molecular mechanism of ergostatrien-3β-ol-mediated hypolipidemic effects. Fenofibrate, a PPARα agonist, has been recommended to reduce circulating triglycerides. In the present invention, fenofibrate displays a decrease of the circulating TG level by 47.9%, while rosiglitazone decreases the circulating TG level less. Ergostatrien-3β-ol shows a moderate reduction in levels of TG. PPARα agonist is known to down-regulate numerous genes involved in lipid synthesis. PPARα ligands (such as fibrates) reduce the expression of apo C-III gene, thus resulting in a hypotriglyceridemic effect. PPARα has been shown to regulate lipid metabolism and fatty acid oxidation. SREBP-1c plays a key role in the activation of lipogenic enzyme expression, fatty acid synthesis and triglyceride accumulation, and it plays the role of PPARα in SREBP-mediated regulation of lipogenic genes. In the present invention, ergostatrien-3β-ol-treated mice display an increase in expressions of PPARα but a reduction in SREBP1c and DGAT2 mRNA. DGAT2 is known to catalyze the final step in the synthesis of triglycerides. Therefore, the down-regulation of DGAT2 seems to be responsible for the hepatic triglyceride output, thus resulting in a decrease in blood TG. These findings further confirm that ergostatrien-3β-ol displays hypolipidemic activity partly via regulation of genes associated with fatty acid oxidation and lipogenesis.

40 mg/kg/day ergostatrien-3β-ol-treated mice show reduced body weight, which primarily reflects decreased fat accumulation with reduced weight of epididymal adipose tissue (EWAT) as well as decreased weight of visceral fat. Although their body weight is lower, 40 mg/kg/day ergostatrien-3β-ol-treated mice show increased skeletal muscle mass. These results reveal that increased Akt signaling resulted in muscle hypertrophy, increased insulin sensitivity, and resistance to HFD-induced weight gain. Akt activation is a common feature of the diverse model of increased insulin sensitivity. Both reduced obesity and increased Akt signaling may elicit the improved insulin sensitivity of the 40 mg/kg/day ergostatrien-3β-ol-treated mice.

Histology investigation has revealed that ergostatrien-3β-ol treatment lowers the area of adipocytes. Because circulating TG level is fluctuating and liver is the major organ responsible for metabolizing fat, presumably ergostatrien-3β-ol reflects the movement of fat from adipose tissue to liver by increasing hepatic lipid metabolism, which leads to reduced adipocyte size and nearly invisible liver lipid droplets.

Ergostatrien-3β-ol decreases blood TC and TG levels while it increased HDL-C concentrations. Moreover, only K3-treated mice display a decrease in LDL-C levels. PPARα agonists are known to reduce LDL-C and increase HDL-C. In the present invention, fenofibrate-treated mice reduce adiposity and displayed no changes in total cholesterol (TC) and LDL-C levels, but increased HDL-C concentrations. The difference between ergostatrien-3β-ol and fenofibrate is that ergostatrien-3β-ol-treated mice show significantly decreased TC levels whereas fenofibrate-treated mice display unchanged levels in this manifest hypercholesterolemia animal model.

In the present invention, ergostatrien-3β-ol-treated mice displays reduced blood TC levels and decreased SREBP2 expression, since SREBP2 plays a major role in the regulation of cholesterol synthesis, implying that the potential mechanism of ergostatrien-3β-ol is involved in SREPB2 on the inhibitory action of cholesterol synthesis. PPARα ligands are used widely to lower serum TG and to increase HDL-C in patients with obesity and dyslipidemia. In the present invention, ergostatrien-3β-ol enhances both HDL-C levels and apo A-I expression. HDL-C is positively associated with a decreased risk of coronary heart disease (CHD). Since apo A-I has been reported to be synthesized by liver cells and the major apolipoproteins of HDL-C are apo A-I and apo A-II, the observed increase in HDL-C level by EK100 is presumably mediated by enhanced hepatic apo A-I production. These results indicate that ergostatrien-3β-ol treatment resulted in elevated HDL-C concentration, a known physiological consequence that may be useful in cardiovascular events.

In summary, ergostatrien-3β-ol and its derivatives from Antrodia camphorata is used to prepare not only a health product for lowering blood glucose levels, but also reducing blood lipids (including circulating triglyceride and total cholesterol, and hepatic total lipid, whereas increasing HDL-C levels. Ergostatrien-3β-ol and its derivatives from mushrooms of Antrodia camphorata is prepared using methanol extraction. The mediated-antihyperlipidemic and antihyperglycemic mechanism demonstrates that the compounds significantly enhance the protein of phosphorylation of AMP-activated protein kinase (p-AMPK) in both skeletal muscular and liver tissue and increased membrane glucose transporter 4 (GLUT4) in skeletal muscle.

Therefore, ergostatrien-3β-ol and its derivatives exhibits not only lowered blood glucose levels accompanied by decreased HbA1c and ameliorated insulin resistance but also diminished blood TC and TG levels. Ergostatrien-3β-ol and its derivatives exerts significantly increased membrane GLUT4 protein in skeletal muscle, which enhances glucose uptake; moreover, ergostatrien-3β-ol and its derivatives increases phosphorylation of AMPK in liver and reduced PEPCK and G6 Pase mRNA levels, which decreases hepatic glucose production, leading to exertion of an antihyperglycemic effect. On the other hand, ergostatrien-3β-ol enhances hepatic expressions of PPARα (fatty acid oxidation) and reduces SREBP1c (lipogenesis), thus resulting in lowering circulating TG levels. Moreover, ergostatrien-3β-ol reduces hepatic expressions of SREBP2 while it enhances apo A-I and thus contributes to a decrease in blood TC and a rise in the plasma HDL-C level. These results reinforce that ergostatrien-3β-ol and its derivatives will have therapeutic potential in treating type 2 diabetes associated with hyperlipidemia.

The present invention provides a method for decreasing mRNA levels of phosphoenol pyruvate carboxykinase (PEPCK), glucose-6-phosphatase (G6 Pase), sterol regulatory element binding protein 1c (SREBP1c), diacylglycerol acyltransferase 2 (DGAT2), apolipoprotein C-III (apo C-III), and SREBP2, but increasing mRNA levels of apolipopretein A-I (apo A-I) and peroxisome proliferator activated receptor α (PPARα) in a cell using ergostatrien-3β-ol and its derivatives; and a method for increasing expression levels of membrane glucose transporter 4 (GLUT4) and phospho-Akt in skeletal muscle tissue, and phospho-AMPK in both skeletal muscle and liver tissue using ergostatrien-3β-ol and its derivatives. Ergostatrien-3β-ol and its derivatives can significantly lower the blood markers, such as blood glucose, glycated hemoglobin (HbA1c), total cholesterol (TC), triglyceride (TG), insulin, and leptin levels in subjects with type 2 diabetes, hyperlipidemia or hepatic total lipids, finally ameliorate insulin resistance. Ergostatrien-3β-ol and its derivatives can significantly ameliorate adipocyte and hepatic ballooning degeneration induced by high-fat-diet to reduce sizes of visceral adipocyte and hepatic ballooning degeneration, ameliorate hyperleptinemia induced by high-fat-diet to reduce blood leptin levels and reduce visceral fat mass and hypertrophy of adipocyte induced by high-fat-diet. Accordingly, the present invention provides a new strategy to treat type 2 diabetes, hyperlipidemia or hepatic total lipids in humans. This strategy has obvious potential commercial applications given the vast amount of products and treatments available on the market to treat type 2 diabetes, hyperlipidemia or hepatic total lipids.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for decreasing mRNA levels of phosphoenol pyruvate carboxykinase (PEPCK), glucose-6-phosphatase (G6 Pase), sterol regulatory element binding protein 1c (SREBP1c), diacylglycerol acyltransferase 2 (DGAT2), apolipoprotein C-III (apo C-III), and SREBP2, but increasing mRNA levels of apolipopretein A-I (apo A-I) and peroxisome proliferator activated receptor .alpha. (PPAR.alpha.) in a cell, comprising contacting the cell with an effective amount of compounds represented by formula (I)

wherein R is a hydrogen atom,

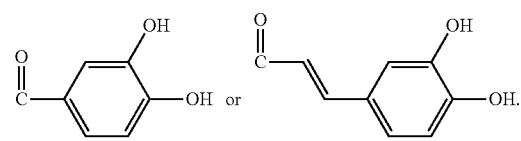 [SMILES: O=Cc1ccc(O)c(O)c1 ; O=C/C=C/c1ccc(O)c(O)c1]

2. The method according to claim 1, wherein the cell is obtained from a subject with a condition of hyperglycemia, hyperlipidemia, hepatic total lipids or ballooning degeneration.

3. A method for increasing expression levels of membrane glucose transporter 4 (GLUT4) in skeletal muscle and phospho-AMPK in both skeletal muscle and liver tissue, comprising contacting the tissue with an effective amount of compounds represented by formula (I)

wherein R is a hydrogen atom

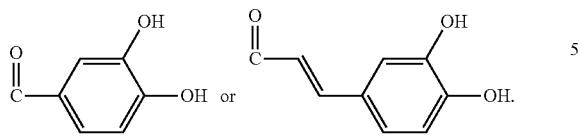

4. The compound according to claim 3, wherein the compounds increase expression levels of phospho-Akt in skeletal muscle to enhance insulin sensitivity.

5. The method according to claim 3, wherein the tissue is obtained from a subject with diabetes.

6. The method according to claim 3, wherein the tissue is obtained from a subject with a condition of hyperlipidemia, dyslipidemia or hepatic total lipids.

7. The method according to claim 3, wherein the compounds are obtained from *Antrodia camphorata*.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
ctacaacttc ggcaaatacc                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tccagatacc tgtcgatctc                                                   20

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
gaacaactaa agcctctgaa ac                                                22

<210> SEQ ID NO 4
<211> LENGTH: 22
<212> TYPE: DNA
<213> ORGANISM: Artificial Sequence
```

```
<220> FEATURE:
<223> OTHER INFORMATION: Synthetic primer

<400> SEQUENCE: 4
ttgctcgata cataaaacac tc                                           22

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
tcttctacaa ccaacagaat ca                                           22

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
gtatcatggt agagaaggaa gc                                           22

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
acctctgttc atgtcagacc                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ataaccacag accaaccaag                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ggctgttgtc taccataagc                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
aggaagaaac gtgtcaagaa                                              20
```

```
<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
agtggcaatg ctatcatcat cgt                                             23

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
aaggaataag tgggaaccag atca                                            24

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
cagttttatc cctagaagca                                                 20

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
tctcacgact caatagctg                                                  19

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
atatcattga aaagcgctac                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
attttcaagt ccacatcact                                                 20

<210> SEQ ID NO 17
<211> LENGTH: 22
<212> TYPE: DNA
<213> ORGANISM: Artificial Sequence
<220> FEATURE:
<223> OTHER INFORMATION: Synthetic primer
```

```
<400> SEQUENCE: 17
acatatatag accagggaag aa                                          22

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
aaactgggac acatagtctc t                                           21

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tgtgtccgtc gtggatctga                                             20

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
cctgcttcac caccttcttg a                                           21
```